(12) United States Patent
Hulliger et al.

(10) Patent No.: US 12,083,315 B2
(45) Date of Patent: Sep. 10, 2024

(54) DRUG DELIVERY DEVICE

(71) Applicant: SENSILE MEDICAL AG, Olten (CH)

(72) Inventors: Thomas Hulliger, Worb (CH); Fabian Bürli, Olten (CH); Frédéric Weibel, Schmitten (CH); Ben Crook, Bremgarten B Bern (CH); Emmanuel Gremion, Echarlens (CH)

(73) Assignee: SENSILE MEDICAL AG, Olten (CH)

( * ) Notice: Subject to any disclaimer, the term of this patent is extended or adjusted under 35 U.S.C. 154(b) by 699 days.

(21) Appl. No.: 17/297,476

(22) PCT Filed: Nov. 27, 2019

(86) PCT No.: PCT/EP2019/082788
§ 371 (c)(1),
(2) Date: May 27, 2021

(87) PCT Pub. No.: WO2020/109409
PCT Pub. Date: Jun. 4, 2020

(65) Prior Publication Data
US 2022/0031940 A1    Feb. 3, 2022

(30) Foreign Application Priority Data

Nov. 30, 2018   (EP) ..................................... 18209397

(51) Int. Cl.
*A61M 5/142*     (2006.01)
*A61M 5/172*     (2006.01)
(52) U.S. Cl.
CPC ........ *A61M 5/14248* (2013.01); *A61M 5/172* (2013.01); *A61M 2005/14268* (2013.01); *A61M 2205/273* (2013.01)
(58) Field of Classification Search
CPC .......... A61M 5/14244; A61M 5/14248; A61M 5/172
See application file for complete search history.

(56) References Cited

U.S. PATENT DOCUMENTS 7,717,903 B2 *   5/2010   Estes ................. A61M 5/14244
                                                              604/890.1
7,726,955 B2    6/2010   Ryser et al.
(Continued)

FOREIGN PATENT DOCUMENTS

CN          1874809        12/2006
CN         102142631        8/2011
(Continued)

OTHER PUBLICATIONS

Written Opinion in International Application No. PCT/EP2019/082788, Jan. 27, 2020, pp. 1-8.
(Continued)

*Primary Examiner* — Laura A Bouchelle
(74) *Attorney, Agent, or Firm* — SALIWANCHIK, LLOYD & EISENSCHENK

(57) ABSTRACT

A drug delivery device (1), comprising a delivery unit (2) in the form of a disposable single use part and a base unit (4) in the form of a reusable part for coupling to the delivery unit (2), the delivery unit comprising a liquid flow system for pumping liquid from a drug vial or cartridge (3) received in the drug delivery device to an outlet of the device for transcutaneous administration of a liquid drug, the base unit including at least a power source and an electronic control system, the delivery unit and base units comprising a releasable locking mechanism including a locking shoulder (30) on the delivery unit that engages a complementary locking shoulder (34) on the base unit. The locking mechanism comprising an unlocking actuator that may be actuated to release the locking shoulder (30) from the complementary locking shoulder (34). The device further comprises a coupling member (8*b*) on the delivery unit that engages a complementary coupling member (8*a*) on the base unit, at least one of the coupling member and complementary coupling member comprising at least one elastic arm (10) with (Continued)

a protuberant portion (11) at a free end thereof, the protuberant portion (11) having a rearwardly inclined taper (13) that engages a complementary taper on a complementary protuberant latch portion (12) of the other of said coupling member and complementary coupling member, configured to provide a pulling force (F) between the base unit and the delivery unit to draw them together in a tight fit without play.

12 Claims, 7 Drawing Sheets

(56) References Cited

U.S. PATENT DOCUMENTS

| | | | |
|---|---|---|---|
| 8,002,567 B2 | 8/2011 | Hara | |
| 8,282,366 B2 | 10/2012 | Hilber et al. | |
| 8,382,700 B2 | 2/2013 | Straessler et al. | |
| 8,957,674 B2 | 2/2015 | Genoud et al. | |
| 9,222,470 B2 | 12/2015 | Genoud et al. | |
| 9,302,285 B2 | 4/2016 | Marbet et al. | |
| 9,592,336 B2 | 3/2017 | Nielsen et al. | |
| 9,662,621 B2 | 5/2017 | Beyer et al. | |
| 9,861,741 B2 * | 1/2018 | Yang | A61M 5/1452 |
| 10,076,605 B2 | 9/2018 | Marbet et al. | |
| 10,143,798 B2 | 12/2018 | Marbet et al. | |
| 10,632,249 B2 | 4/2020 | Marbet et al. | |
| 10,954,928 B2 | 3/2021 | Burli et al. | |
| 11,009,018 B2 | 5/2021 | Wyss et al. | |
| 11,009,026 B2 | 5/2021 | Girschweiler et al. | |
| 11,022,107 B2 | 6/2021 | Brandt et al. | |
| 11,160,922 B2 | 11/2021 | Just | |
| 11,612,687 B2 | 3/2023 | Marbet | |
| 11,744,940 B2 | 9/2023 | Wieser et al. | |
| 2006/0271020 A1 | 11/2006 | Huang et al. | |
| 2008/0294094 A1 | 11/2008 | Mhatre et al. | |
| 2009/0030382 A1 | 1/2009 | Brandt et al. | |
| 2010/0241063 A1 | 9/2010 | Straessler et al. | |
| 2012/0046651 A1 | 2/2012 | Beyer et al. | |
| 2014/0231549 A1 | 8/2014 | Thiemer et al. | |
| 2016/0158436 A1 | 6/2016 | Yang | |
| 2016/0339172 A1 | 11/2016 | Michaud et al. | |
| 2017/0056582 A1 | 3/2017 | Niklaus | |
| 2018/0085517 A1 | 3/2018 | Laurence et al. | |
| 2023/0398289 A1 | 12/2023 | Wieser et al. | |
| 2024/0033422 A1 | 2/2024 | Büchi et al. | |
| 2024/0033423 A1 | 2/2024 | Muller et al. | |
| 2024/0066541 A1 | 2/2024 | Perrier et al. | |

FOREIGN PATENT DOCUMENTS

| | | |
|---|---|---|
| CN | 103714879 | 4/2014 |
| WO | WO 02/068015 | 9/2002 |
| WO | WO 2005/039674 | 5/2005 |
| WO | WO 2008/024808 | 2/2008 |
| WO | WO 2009/117466 | 9/2009 |
| WO | WO 2015/015379 | 2/2015 |
| WO | WO 2015/114373 | 8/2015 |
| WO | WO 2017/177094 | 10/2017 |
| WO | WO 2018/166699 | 9/2018 |

OTHER PUBLICATIONS

Claims as filed in U.S. Appl. No. 18/281,784, filed Sep. 13, 2023, pp. 1-4.

Claims as filed in U.S. Appl. No. 18/281,785, filed Sep. 13, 2023, pp. 1-4.

Claims as filed in U.S. Appl. No. 18/281,970, filed Sep. 14, 2023, pp. 1-4.

Claims as filed in U.S. Appl. No. 18/281,971, filed Sep. 14, 2023, pp. 1-3.

Claims as filed in U.S. Appl. No. 18/462,457, filed Sep. 7, 2023, pp. 1-3.

Claims as filed in U.S. Appl. No. 18/460,719, filed Sep. 5, 2023, pp. 1-3.

Claims as filed in U.S. Appl. No. 18/460,722, filed Sep. 5, 2023, pp. 1-3.

Claims as filed in U.S. Appl. No. 18/489,887, filed Oct. 19, 2023, pp. 1-3.

Claims as filed in U.S. Appl. No. 18/389,242, filed Nov. 14, 2023, pp. 1-3.

* cited by examiner

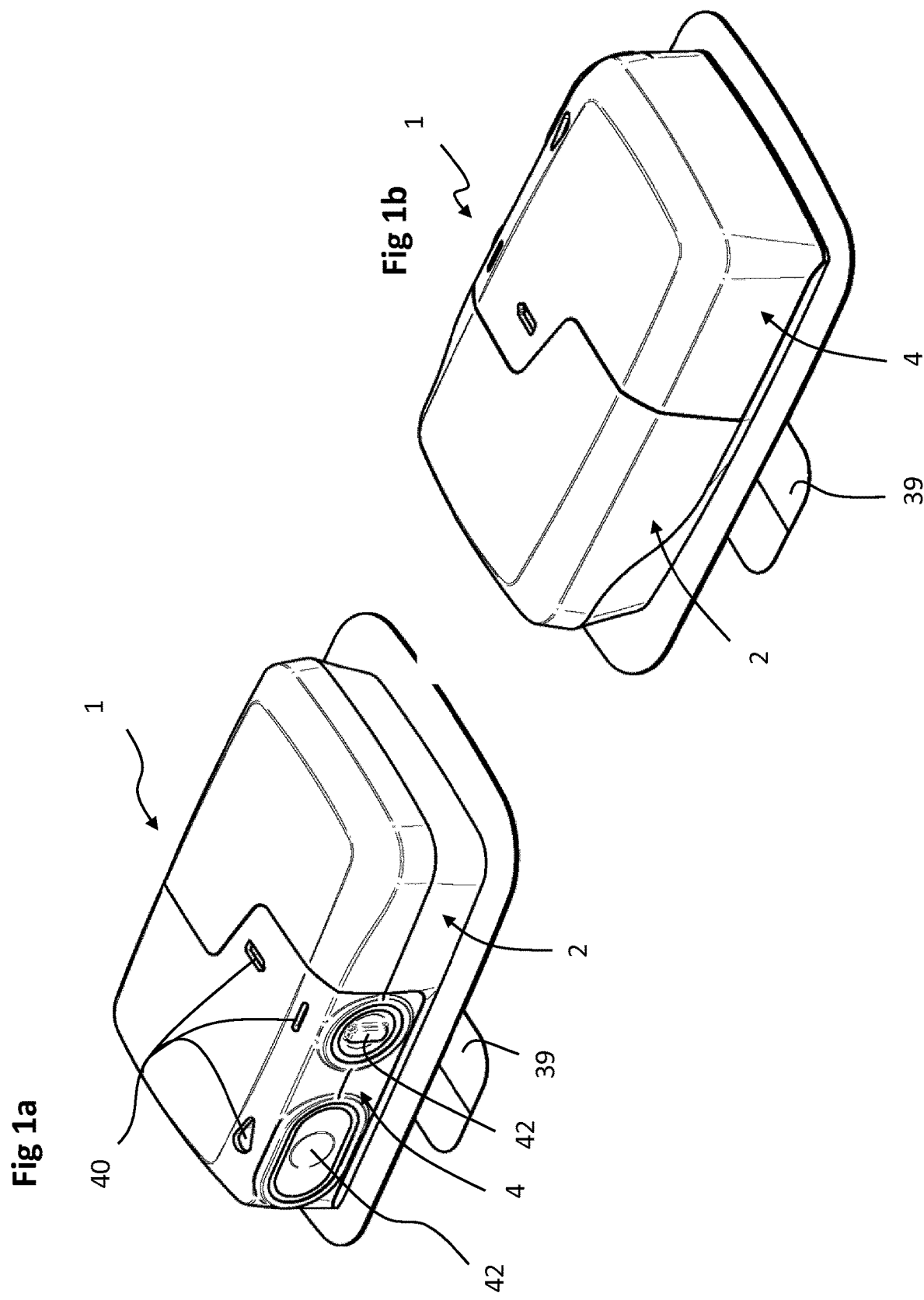

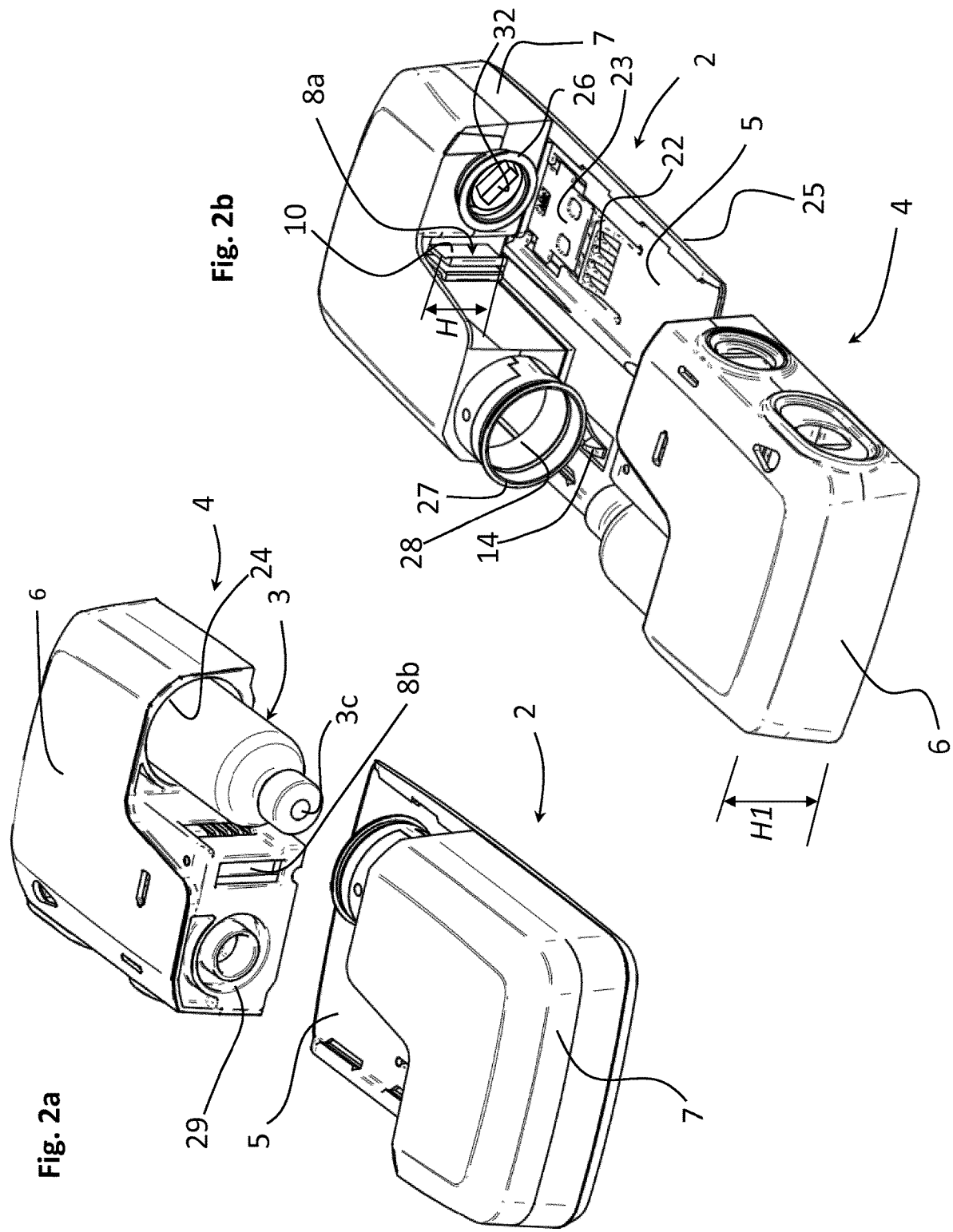

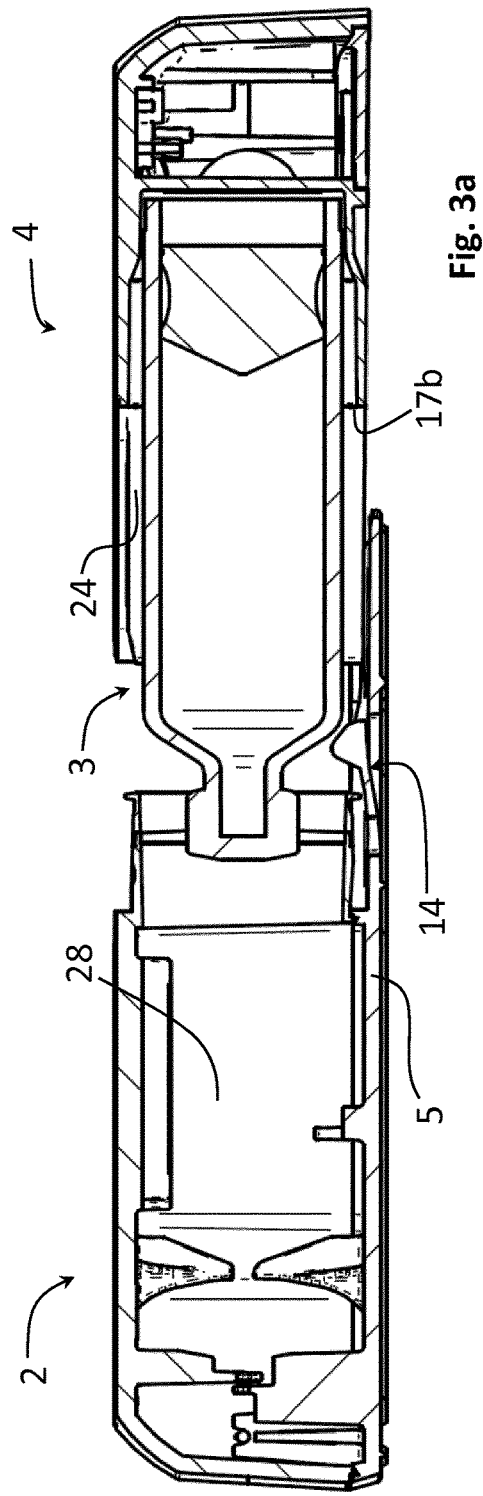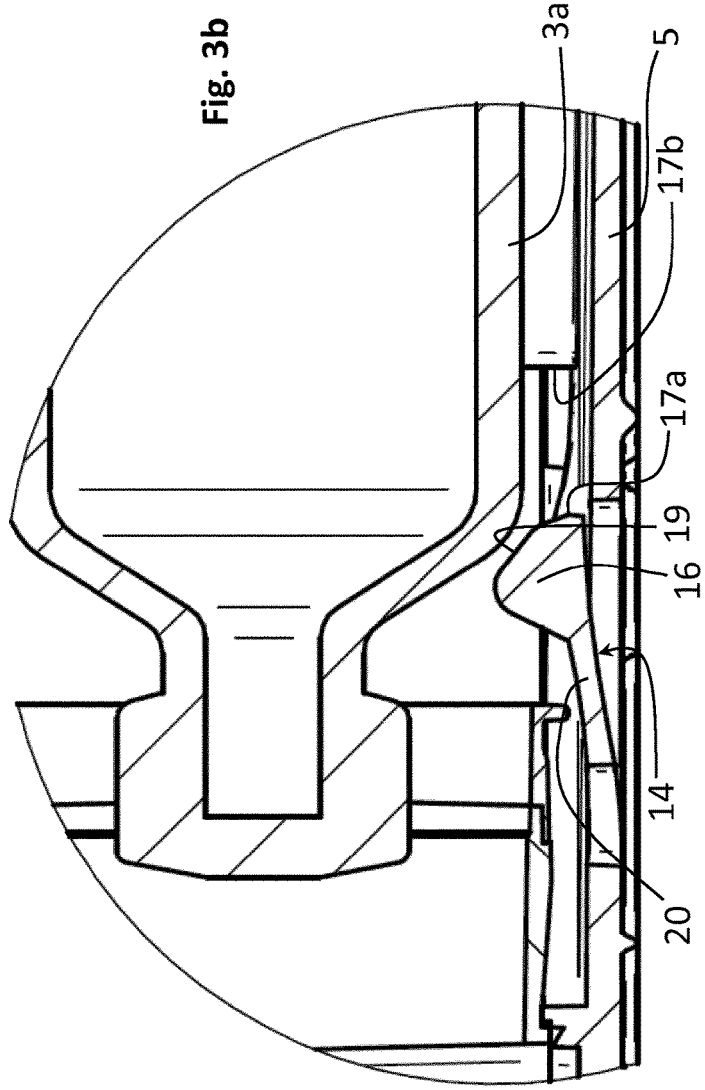

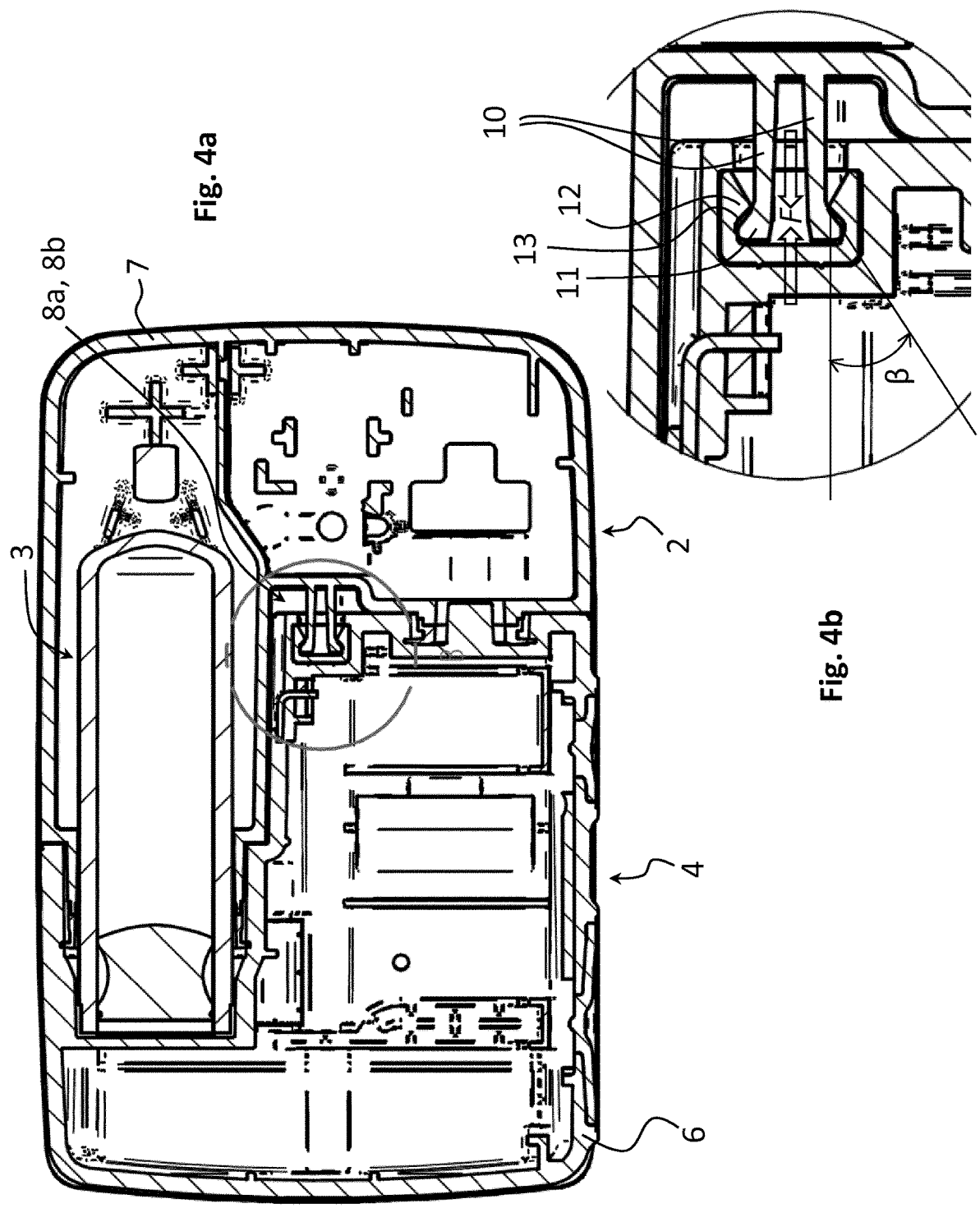

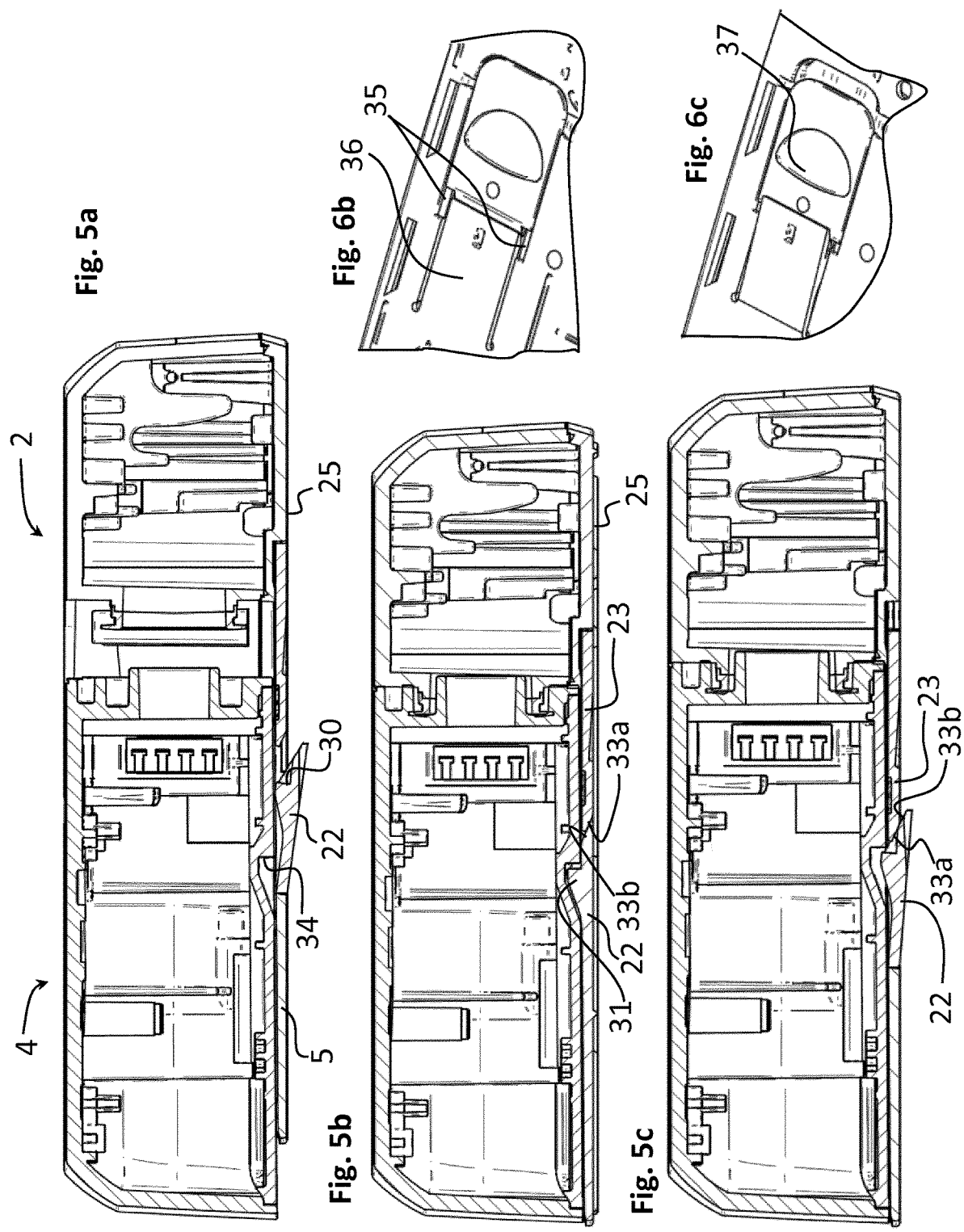

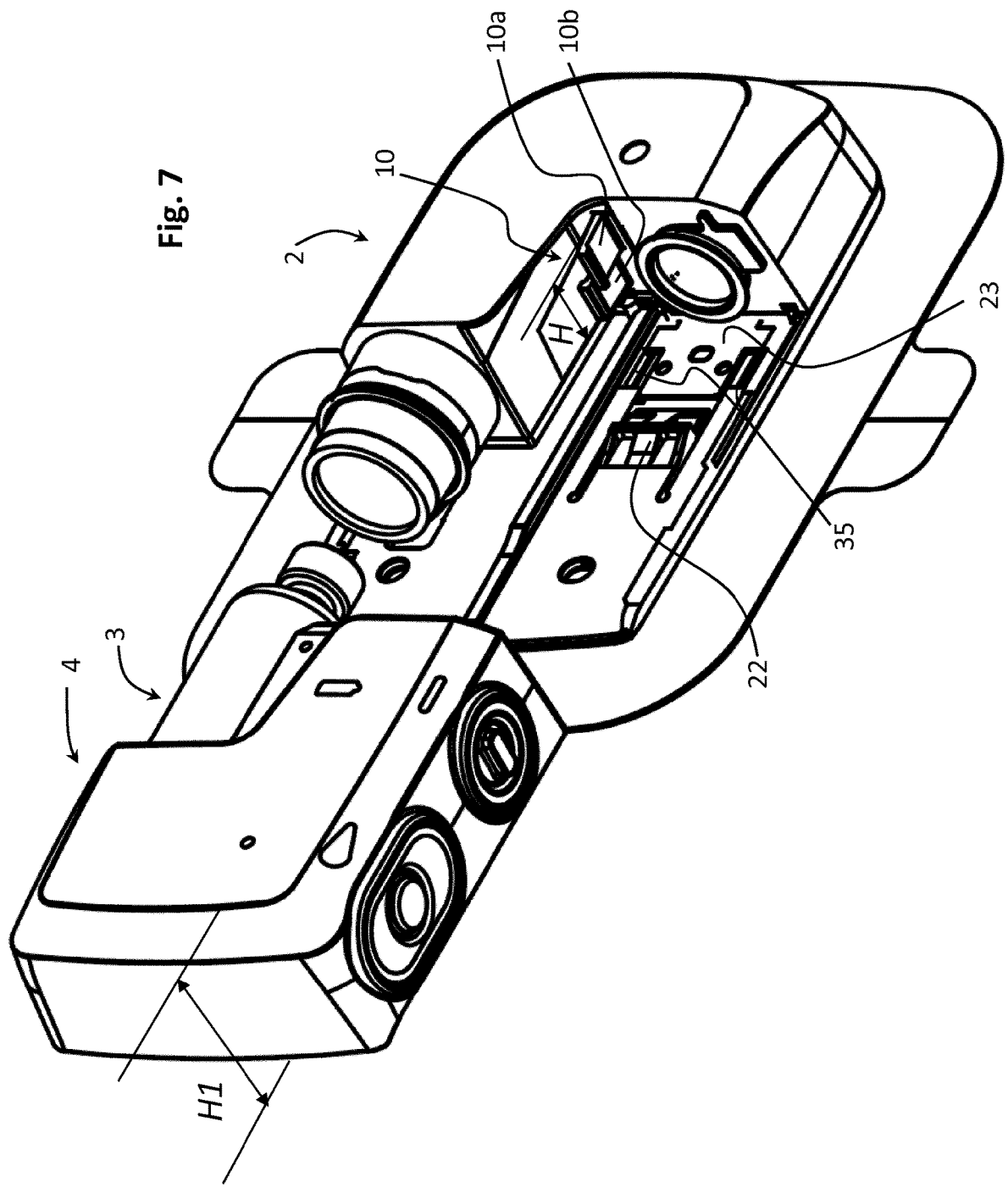

DRUG DELIVERY DEVICE

CROSS-REFERENCE TO RELATED APPLICATION

This application is the U.S. national stage application of International Patent Application No. PCT/EP2019/082788, filed Nov. 27, 2019.

TECHNICAL FIELD

This invention relates to a drug delivery device for transcutaneous administration of a liquid drug. The invention in particular relates to a drug delivery device in the form of a patch device with reusable and single use disposable components.

DESCRIPTION OF RELATED ART

A drug delivery device in a form of a patch device for mounting on a patient's skin for transcutaneous delivery of liquid drug is described for instance in WO2015015379. Patch devices for transcutaneous delivery of a liquid drug that comprise a reusable unit and a disposable unit typically receive a cartridge or vial containing the liquid drug to be administered. The liquid drug may for instance be insulin or other drugs that are administered multiple times in a basal rate and/or bolus dose over a certain period of treatment time. For such conditions, it is well-known to provide the drug delivery device in two separable portions, one reusable portion containing electronics, a power supply and a drive mechanism, the other single use disposable part comprising a transcutaneous delivery mechanism with a needle, an adhesive patch for mounting against the patient's skin, and the drug pumping and liquid flow circuit that may only be used for a limited period of time and that needs to be replaced once consumed or after a certain period of time. In the drug delivery device described in the afore-mentioned publication, a pump engine is included in the disposable part, the motor for providing the torque for driving the rotor of the pump engine being provided in the reusable unit and coupling mechanically to the pump engine rotor when the disposable and reusable units are mounted together.

When assembling the disposable and reusable units, the patient or healthcare practitioner needs to insert a drug cartridge or vial prior to assembly of the reusable and disposable units. The drug vial typically comprises a septum that is pierced by a needle within the disposable unit when the drug vial is inserted in the disposable unit. It can happen however that sometimes the user forgets to place a drug vial before assembling the disposable and reusable unit and this can lead to having to disassemble the units and to throw away the disposable unit and replace it with new one.

The disposable and reusable units are held together by a latch system that may be actuated by the user to disassemble the units. To prevent the two units from inadvertently releasing and separating, the locking system is designed with catches and shoulders that lock together and cannot be released by pulling apart the two units, unless a button or other form of actuator is actuated by the user. The locking edges should therefore be at an angle that prevents them slipping with respect to each other to the open position when a traction force pulling apart the reusable and disposable units is applied. Such locking mechanisms however may allow a slight amount of play between the disposable and reusable units. The tolerances and play required for the locking system however may reduce the quality of the sealing between the disposable and reusable units. Moreover, since the reusable unit may be used many times the catch surfaces of the locking mechanism may be subject to some wear thus increasing tolerances and worsening the afore-mentioned situations.

When a drug delivery device is used as a patch unit, the patient may in certain applications carry the device for a few days and may perform sport or take a shower while carrying the device and therefore the device should be resistant to environmental conditions. More generally, any play between the two components can affect functioning in an adverse manner and renders the device more easily prone to damage and malfunctioning. An accurate repeatable fit between units is therefore important.

SUMMARY OF THE INVENTION

In view of the foregoing, it is an object of the invention to provide a drug delivery device, in particular in the form of a patch device, with reusable and disposable units for administration of a liquid drug provided in a separate drug vial or cartridge, that is robust and reliable.

It is advantageous to provide a drug delivery device that reduces the risk of false manipulation by a user in particular when assembling the device.

It is advantageous to provide a drug delivery device that is compact and easy to use.

It is advantageous to provide a drug delivery device that is economical to produce.

It is advantageous to provide a drug delivery device that is comfortable to wear and easy to use.

Disclosed herein is a drug delivery device, comprising a delivery unit in the form of a disposable single-use part and a base unit in the form of a reusable part for coupling to the delivery unit, the delivery unit comprising a liquid flow system for pumping liquid from a drug vial or cartridge received in the drug delivery device to an outlet of the device for transcutaneous administration of a liquid drug, the base unit including at least a power source and an electronic control system.

The delivery unit and base units may comprise a releasable locking mechanism including a locking shoulder on the delivery unit that engages a complementary locking shoulder on the base unit. The locking mechanism may comprise an unlocking actuator that may be actuated to release the locking shoulder from the complementary locking shoulder.

The delivery unit comprises a housing that may have a base wall defining a mounting face, and a liquid flow system for pumping liquid from a drug vial or cartridge received in the drug delivery device to an outlet of the device for transcutaneous administration of a liquid drug.

In a first aspect of the invention, the device further comprises a coupling member on the delivery unit that engages a complementary coupling member on the base unit, at least one of the coupling member and complementary coupling member comprising at least one elastic arm with a protuberant portion at a free end thereof, the protuberant portion having a rearwardly inclined taper that engages a complementary taper on a complementary protuberant latch portion of the other of said coupling member and complementary coupling member. The coupling members are configured to provide a pulling force between the base unit and the delivery unit to draw them together in a tight fit without play.

In a second aspect of the invention, the housing of the delivery unit is provided with a cartridge check finger that comprises a protuberance mounted on an elastic arm, the protuberance arranged to engage a portion of the drug vial when it is inserted in a cavity of the delivery device. The cartridge check finger comprises a blocking shoulder arranged to engage a blocking shoulder on the base unit to prevent full coupling of the delivery unit to the base unit when a drug vial is not inserted in said cavity of the delivery device.

In an advantageous embodiment, the at least one elastic arm is provided on the delivery unit and the complementary protuberant latch portion is provided on the base unit.

In an advantageous embodiment, the at least one of the coupling member and complementary coupling member comprises at least two said elastic arms arranged to elastically bias towards each other and to engage at least two said complementary protuberant latch portions.

In an advantageous embodiment, the taper is provided at an angle of inclination with respect to the direction of the pulling force in the range of 30° to 60°, more preferably in the range of 35° to 45°.

In an advantageous embodiment, an overall height of the elastic arms is greater than 50% of an overall height of the drug delivery device, as measured perpendicularly from a mounting face.

In an advantageous embodiment, the locking shoulder on the delivery unit is provided on an elastic beam integrally formed in a base wall of the delivery unit.

In an advantageous embodiment, the unlocking actuator is slidably mounted on the base wall movable from a locked position to an unlocking position, the unlocking actuator comprising a cam edge engageable with the elastic beam to displace the beam such that the locking shoulder disengages the complementary locking shoulder.

In an advantageous embodiment, the slidable unlocking actuator is received in an orifice of the base wall and slidable within the plane of the base wall.

In an advantageous embodiment, the cartridge check finger is mounted on the base wall and when a drug vial is not inserted in said cavity of the delivery device, projects above an inner side of the base wall.

In an advantageous embodiment, the cartridge check finger is integrally formed with the base wall, which may for instance be made by injection molding of a polymer material.

In an advantageous embodiment, the cartridge check finger is in the form of a cantilever elastic beam integrally molded with the base wall.

Further objects and advantageous features of the invention will be apparent from the claims, from the detailed description, and annexed drawings, in which:

BRIEF DESCRIPTION OF THE DRAWINGS

FIGS. 1a and 1b are perspective views taken on opposite sides of a drug delivery device according to an embodiment of the invention;

FIGS. 2a to 2c are perspective views of the device of FIGS. 1a and 1b (with some parts such as the adhesive base peel off layer removed for convenience) showing the disposable and reusable units uncoupled;

FIG. 3a is a side cross-sectional view of the embodiment of FIGS. 2a-2c, the section taken longitudinally through the drug vial with the disposable and reusable units about to be coupled together;

FIG. 3b is an enlarged view of a portion of FIG. 3a;

FIG. 4a is a top cross-sectional view of the embodiment of FIGS. 2a-2c with the disposable and reusable units coupled together;

FIG. 4b is an enlarged view of a portion of FIG. 4a;

FIG. 5a is a side cross-sectional view of an embodiment of the drug delivery device with the base and delivery units in the process of being coupled together;

FIG. 5b is a side cross-sectional view of the embodiment of FIG. 5a with the base and delivery units fully coupled together; and FIG. 5c is a side cross-sectional view of the embodiment of FIG. 5b showing a locking latch actuator moved towards a release position to uncouple the base and delivery units;

FIG. 6b is a view of part of the base wall of the device showing the locking mechanism in the position of FIG. 5b;

FIG. 6c is a view of part of the base wall of the device showing the locking mechanism in the position of FIG. 5c;

FIG. 7 is a perspective view of a drug delivery device according to another embodiment of the invention showing the disposable and reusable units uncoupled.

DETAILED DESCRIPTION OF EXEMPLARY EMBODIMENTS

Figure 2C:
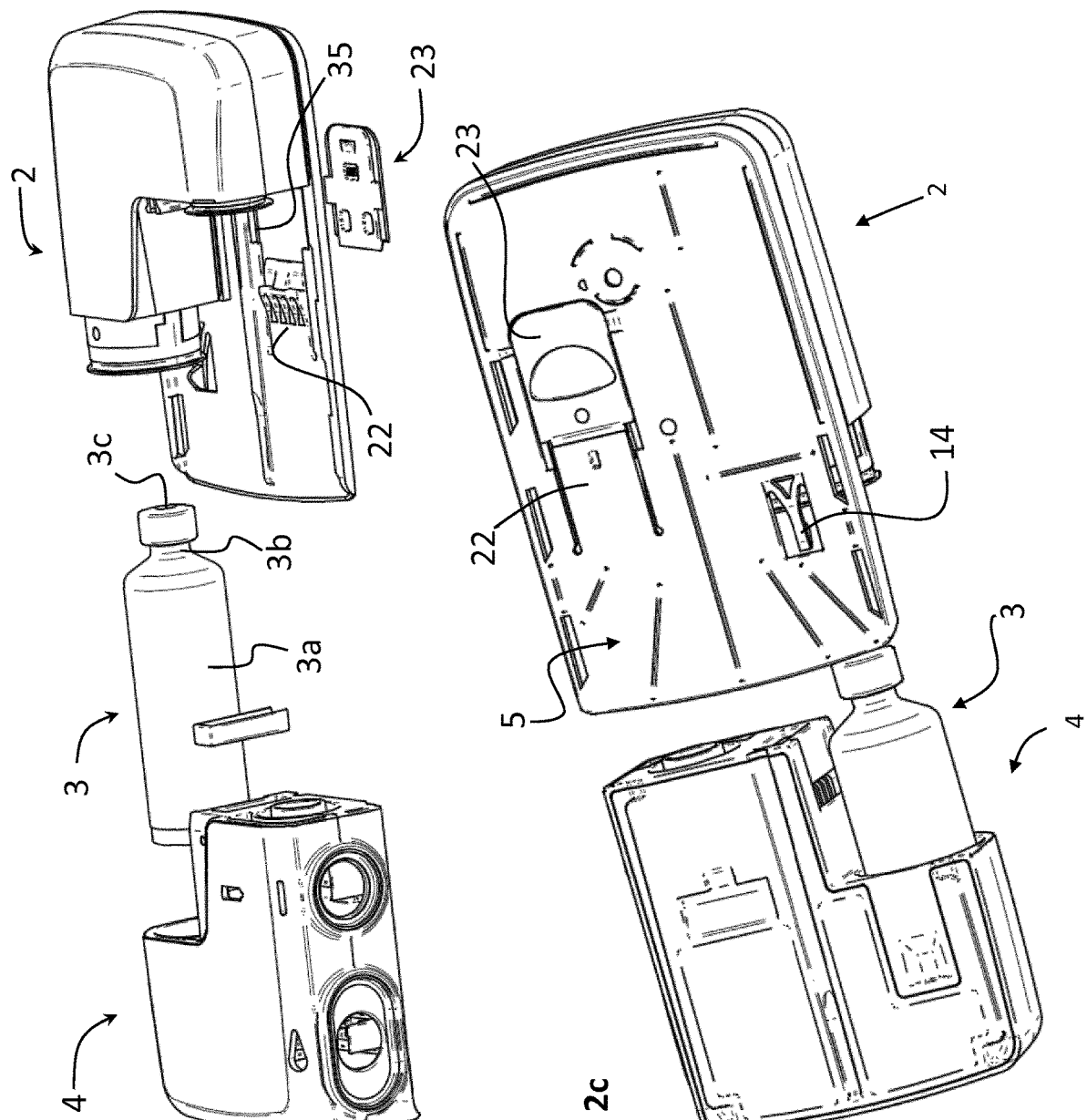

Referring to the figures, a drug delivery device 1 comprises a delivery unit 2 and a base unit 4. The delivery unit 2 is a single use disposable unit 2 and is removably connected to the base unit 4 which is re-usable with a plurality of successive delivery units. The delivery unit may be used for a single administration of a drug, or for use over a few days for a continuous or intermittent delivery of a drug. For instance, for the administration of a drug such as insulin, the drug delivery device may be configured as a patch device for mounting on a patient's skin over a period of a few days to a few weeks for a basal rate and bolus administration of the drug. Once the vial is empty or the duration of use of the delivery unit has reached the specified lifetime, the delivery unit is thrown away and a new delivery unit may be mounted to the base unit for a new cycle of drug administration.

The delivery unit 2 comprises a drug flow system including a subcutaneous delivery mechanism (not shown) to deliver a fluid trans-dermally or to a catheter and a pump (not shown) to transfer a liquid drug contained in a drug cartridge or vial to the subcutaneous delivery mechanism via a liquid flow circuit, and a cavity 28 to lodge the drug cartridge or vial 3, and a support member or housing 7 for supporting the aforementioned components.

The reusable base unit 4 comprises a pump drive (not shown), a battery (not shown), an electronic control unit (not shown) and a housing 6. The base unit housing 6 may comprise a cavity 24 lodging a portion of the drug cartridge or vial 3 when coupled to the delivery unit 2 and optionally comprises one or more sensors (not shown) for detecting the drug fill level of the reservoir. The reusable device may comprise a user interface including command buttons 42 and status lights or other indicators 40 to allow the user to enter commands and to provide information on the status and operation of the device 1.

The pump module is operable to pump fluid from the drug cartridge 3 to a needle (not shown) for subcutaneous delivery. In this example the pump module comprises a drive interface 32 configured to couple rotationally with a pump drive mounted in the base unit 4 such that torque from the pump drive is transferred to the pump module to drive a rotor of the pump in rotation. A suitable pump engine and drive unit is provided in WO 2005/039674, which is incorporated herein by reference. However, it will be appreciated that other rotary pump engines and pump drives may be used. In a variant, a portion of the motor could be incorporated in the delivery unit 2 and receive power, for instance via electrical contacts or by induction from a power source (not shown) mounted in the base unit 4.

In an embodiment, the disposable delivery unit is provided with an adhesive base covered by a protective film 39 that may be peeled off to place the adhesive mounting surface 25 of the base 5 against the patient's skin. It may however be noted that in other embodiments, the base wall may be provided without an adhesive layer and the device placed against the patient's skin by other means for instance by means of a strap or band encircling the patient's body portion against which the drug delivery device is placed.

The delivery unit 2 and base unit may be locked together with a releasable locking mechanism. As best seen in FIGS. 5*a*-6*c*, the locking mechanism, in the illustrated embodiment, comprises a locking latch 22 positioned in the base wall 5 of the delivery unit 2, the locking latch having a locking shoulder 30 that engages a complementary locking shoulder 34 in the base unit once the reusable and disposable units 4, 2 are fully mounted together. The locking latch 22 engaging the locking shoulder 34 of the base unit 4 ensures that the base unit 4 and delivery unit 2 are securely locked together when in use. In order to uncouple the delivery and base units, an unlocking actuator 23 is movably mounted on the base wall 5. In the illustrated embodiment, the unlocking actuator 23 is slidably mounted on the base wall 5 and can be moved from a locked position as shown in FIGS. 5*b* and 6*b* to an unlocking position as shown in FIGS. 5*c* and 6*c*. In the unlocking position, a tapered cam edge 33*a* of the unlocking actuator 23 engages a tapered cam edge 33*b* of the locking latch 22 to displace the locking latch such that the locking shoulder 30 disengages the complementary locking shoulder 34 of the base unit 4. In the illustrated embodiment, the locking latch 22 may advantageously be integrally formed with the base wall 5 and be for instance in the form of a beam 36 that can move elastically and pivotally with respect to the base wall substantially orthogonally to the plane of the base wall. Thus, when the base unit 4 is slid over the base wall 5 of the delivery unit 2, the locking protrusion 30 of the locking latch 22 is elastically biased downwardly until the locking shoulder 30 passes the complementary locking shoulder 34 in the base unit where it snaps back into the locking position as shown in FIGS. 5*b* and 6*b*.

The slidable unlocking actuator 23 may be in the form for instance of a plastic part, that is slidably guided by rails 35 formed as edges of an orifice of the base wall 5. In the illustrated embodiment, the unlocking actuator is essentially slidable within the plane of the base wall 5. A fingergrip 37 may be provided on the outer mounting surface of the unlocking actuator 23 in order to enable the actuator 23 to be pushed with a user's finger to slide the actuator 23 to the unlocking position.

It may be noted that if the mounting surface 25 is provided with an adhesive layer, the adhesive layer would preferably not cover the unlocking actuator 23 to allow the unlocking actuator to be actuated.

The delivery unit 2 further comprises a coupling member 8*b* that engages a complementary coupling member 8*a* of the base unit as best seen in FIGS. 2*a*, 2*b* and 4*a*, 4*b*. The coupling member 8*a*, 8*b* also provides a latching function between the base unit 4 and the delivery unit 2. The latching function provided by the coupling members 8*a*, 8*b* is however configured to draw the base unit 4 and delivery unit 2 into a tight coupling against each other to eliminate play and ensure accurate coupling of the two parts together and good sealing where provided. In this regard, at least one of the delivery unit 2 and base unit 4 is provided with elastic arms 10 provided with a protuberant latch portion 11 at a free end thereof, the latch portion 11 having a rearwardly inclined taper 13 that engages a complementary taper on a protuberant latch portion 12 of the base unit 4 also provided with a taper 13. The tapers 13 are configured to provide a pulling force F between the housings of the base unit and the delivery unit to draw them together in a tight fit without play.

The coupling member 8*b* of the base unit 4 is in the illustrated embodiment in the form of a cavity with the protuberant latch portions arranged on opposite sides of the cavity that elastically bias the air of elastic arms 10 as the protuberant latch portions thereof pass between the latch protuberances 12 of the cavity. The taper 13 is provided at an angle of inclination β with respect to the direction of the traction force F that allows the elastic arms 10 to bias towards each other when the delivery and base units 2, 4 are pulled apart to allow uncoupling of the base and delivery units. Preferably, the angle of inclination β is in the range of 30° to 60°, more preferably in the range of 35° to 45°.

The overall height H of the elastic arms 10 may advantageously be greater than 50% of the overall height H1 of the drug delivery device, as measured perpendicularly from the mounting face 25, to ensure a robust and strong traction between the coupled delivery and base units. The elastic arms 10 of the coupling member 8*a*, 8*b* are preferably provided on the disposable delivery unit 2 since they are inherently more fragile than the corresponding cavity of the base unit.

In the variant of FIG. 2*b*, each elastic arm of the pair of arms has the same height corresponding to the overall height H. In the variant of FIG. 7, each elastic arm 10*a*, 10*b* has a height that is about 50% of the overall height H, the arms being offset with respect to each other such that they do not overlap. The latter configuration facilitates the molding of the latch arms.

Uncoupling of the base and delivery units is thus performed by sliding the unlocking actuator 23 to the unlocked position and pulling apart the base unit 4 and delivery unit 2. The above described configuration ensures both a secure locking of the base unit to the delivery unit when the device is in use, while also ensuring a tight fit without play between the two units.

The use of a standard drug vial or cartridge 3 in a drug delivery device is in many circumstances advantageous. In the illustrated embodiment, the drug vial 3 has generally a cylindrical reservoir portion 3*a* that at one end tapers to a neck 3*b* with an outlet that is covered by a septum 3*c* that is pierced by a hollow needle in the delivery unit 2. Such configurations for accessing the liquid within the drug vial are per se known and do not need to be further described. The drug vial 3 may, during the mounting process prior to use, be either mounted in the cavity 24 of the base unit 4 as illustrated in FIG. 1*b*, with the septum end 3*c* facing the cavity 28 of the delivery unit 2, or the drug vial may be inserted first into the cavity 28 of the delivery unit and the base unit then assembled to the delivery unit with the already installed drug cartridge 3.

In order to ensure that the base unit 4 may not be locked to the delivery unit 2 unless there is a drug vial 3 installed, the housing 7 of the delivery unit is provided with a cartridge check finger 14 that comprises a protuberance 16 mounted on an elastic arm 20 as best seen in FIGS. 3*a* and 3*b*. In an advantageous embodiment, the protuberance and elastic arm may be integrally formed with the base wall 5 which may for instance be made by injection molding of a polymer material. The protuberance 16 projects above an inner side of the base wall 5 to an extent that ensures engagement with the cylindrical portion 3a of the drug vial 3 when it is inserted in the cavity 28 of the delivery device.

The protuberance 16 may be provided with an inclined engagement surface 19 to smoothly bias towards the base wall 5 when the drug vial 3 is inserted into the cavity 28. The cartridge check finger 14 is provided at its free end with a blocking shoulder 17a that is positioned above the inner side of the base wall 5 configured to engage a blocking shoulder 17b forming part of the base unit 4 when the base unit is slid from the uncoupled towards the coupled position with the delivery unit.

In the absence of a drug vial the cartridge check finger 14 is positioned such that the blocking shoulder 17b during coupling of the delivery and base units abuts against the blocking shoulder 17a of the check finger and prevents further coupling. In the presence of a drug vial 3, the check finger 14 is downwardly biased towards the base wall 5 such that the blocking shoulder 17a does not engage the blocking shoulder 17b, whereby the blocking shoulder 17b may engage the inclined engagement surface 19 to further bias the check finger 14 out of the way and allow the delivery unit 2 and base unit 4 to be fully assembled together.

In the illustrated embodiment, the check finger 14 is illustrated in the form of essentially a cantilever elastic beam integrally molded with the base wall 5, however other elastically mounted members that have a blocking shoulder that is biased out of the way of a complementary blocking shoulder on the base unit may be provided.

A particularly simple yet effective means of ensuring that the base unit is not mounted to the delivery unit without a drug vial being installed herein is therefore provided in a simple and cost-effective manner.

LIST OF FEATURES

Drug delivery device 1
  Delivery unit 2 (disposable part)
    Housing 7
      Base wall 5
        Mounting surface 25
        edge rails 35
        protective film 39
      Coupling member 8a
        Elastic arms 10
        Latch portion 11
          Taper 13
      Cartridge check finger 14
        Elastic arm 20
        Protuberance 16
          Inclined engagement surface 19
        Blocking shoulder 17a
    Locking latch 22
      Elastic beam 36
      Locking protrusion 31
      Locking shoulder 30
      camming edge 33b
    Unlocking actuator 23
      Finger grip 37
      camming edge 33a
    Pump sealing interface 26
    Cartridge receiving cavity 28
      Sealing interface 27
    Liquid flow system (not shown)
      Pump module (not shown)
        Drive interface 32
    Transcutaneous delivery system (not shown)
  Base unit 4 (reusable part)
    Housing 6
      Cartridge receiving cavity 24
      Coupling member 8b
        Latch portion 12
          Taper 13
        Blocking shoulder 17b
      Base wall
        Complementary locking shoulder 34
    Electronic control system (not shown)
    Power source (battery)
    Pump drive (not shown)
      Coupling interface 29
    Command buttons 42
    Status lights or other indicators 40
  Drug cartridge 3
    Cylinder portion 3a
    Neck portion 3b
    Septum 3c

The invention claimed is:

1. A drug delivery device, comprising a delivery unit in the form of a disposable single-use part and a base unit in the form of a reusable part for coupling to the delivery unit, the delivery unit comprising a liquid flow system for pumping liquid from a drug vial or cartridge received in the drug delivery device to an outlet of the device for transcutaneous administration of a liquid drug, the base unit including at least a power source and an electronic control system, the delivery unit and base units comprising a releasable locking mechanism including a locking shoulder on the delivery unit that engages a complementary locking shoulder on the base unit, the locking mechanism comprising an unlocking actuator that may be actuated to release the locking shoulder from the complementary locking shoulder, wherein the device further comprises a coupling member on the delivery unit that engages a complementary coupling member on the base unit, at least one of the coupling member and complementary coupling member comprising at least one elastic arm with a protuberant portion at a free end thereof, the protuberant portion having a rearwardly inclined taper that engages a complementary taper on a complementary protuberant latch portion of the other of said coupling member and complementary coupling member, configured to provide a pulling force (F) between the base unit and the delivery unit to draw them together in a tight fit without play.

2. The drug delivery device of claim 1, wherein said at least one elastic arm is provided on the delivery unit and said complementary protuberant latch portion is provided on the base unit.

3. The drug delivery device of claim 1, wherein said at least one of the coupling member and complementary coupling member comprises at least two said elastic arms arranged to elastically bias towards each other and to engage at least two said complementary protuberant latch portions.

4. The drug delivery device of claim 1, wherein the taper is provided at an angle of inclination (β) with respect to the direction of the pulling force (F) in the range of 30° to 60°, more preferably in the range of 35° to 45°.

5. The drug delivery device of claim 1, wherein an overall height (H) of the elastic arms is greater than 50% of an overall height (H1) of the drug delivery device, as measured perpendicularly from a mounting face.

6. The drug delivery device of claim 1, wherein and the locking shoulder on the delivery unit is provided on an elastic beam integrally formed in a base wall of the delivery unit.

7. The drug delivery device of claim 1, wherein the unlocking actuator is slidably mounted on the base wall movable from a locked position to an unlocking position, the unlocking actuator comprising a cam edge engageable with the elastic beam to displace the beam such that the locking shoulder disengages the complementary locking shoulder.

8. The drug delivery device of claim 7, wherein the slidable unlocking actuator is received in an orifice of the base wall and slidable within the plane of the base wall.

9. The drug delivery device of claim 1, wherein the delivery unit comprises a housing with a base wall defining a mounting face of the device, the delivery unit comprising a cartridge check finger that comprises a protuberance mounted on an elastic arm, the protuberance arranged to engage a portion (3a) of the drug vial when it is inserted in a cavity of the delivery device, the cartridge check finger comprising a blocking shoulder arranged to engage a blocking shoulder on the base unit to prevent full coupling of the delivery unit to the base unit when a drug vial is not inserted in said cavity of the delivery device.

10. The drug delivery device of claim 9, wherein the cartridge check finger is mounted on the base wall and when a drug vial is not inserted in said cavity of the delivery device, projects above an inner side of the base wall.

11. The drug delivery device of claim 9, wherein the cartridge check finger is integrally formed with the base wall.

12. The drug delivery device of claim 9, wherein the cartridge check finger is in the form of a cantilever elastic beam integrally molded with the base wall.

* * * * *